United States Patent
Wang et al.

(10) Patent No.: US 10,138,501 B2
(45) Date of Patent: Nov. 27, 2018

(54) METHOD FOR PREPARING DIGLYCERIDE USING BUBBLE COLUMN REACTOR

(71) Applicant: JINAN UNIVERSITY, Guangdong (CN)

(72) Inventors: Yong Wang, Guangdong (CN); Yinglai Teng, Guangdong (CN); Manman Liu, Guangdong (CN); Ning Zhang, Guangdong (CN)

(73) Assignee: Jinan University, Guangzhou, Guangdong Province (CN)

(*) Notice: Subject to any disclaimer, the term of this patent is extended or adjusted under 35 U.S.C. 154(b) by 0 days.

(21) Appl. No.: 15/503,226

(22) PCT Filed: Jul. 24, 2015

(86) PCT No.: PCT/CN2015/085057
§ 371 (c)(1),
(2) Date: Feb. 10, 2017

(87) PCT Pub. No.: WO2016/023413
PCT Pub. Date: Feb. 18, 2016

(65) Prior Publication Data
US 2017/0233776 A1    Aug. 17, 2017

(30) Foreign Application Priority Data
Aug. 13, 2014 (CN) .......................... 2014 1 0397931

(51) Int. Cl.
C12P 7/64 (2006.01)
(52) U.S. Cl.
CPC ............... *C12P 7/6454* (2013.01); *C12P 7/64* (2013.01); *C12Y 301/01003* (2013.01)
(58) Field of Classification Search
CPC .................................................. C12P 7/6454
See application file for complete search history.

(56) References Cited

FOREIGN PATENT DOCUMENTS

| CN | 102272317 A | 12/2011 |
| CN | 102304552 A | 1/2012 |
| CN | 102517348 A | 6/2012 |
| CN | 104178530 A | 12/2014 |

OTHER PUBLICATIONS

Yeh et al. JAOCS, 1998, 75(5):643-650.*
Weber et al. J. Agric. Food Chem., 2004, 52:5347-5353.*
International Search Report for Publication No: WO 2016/023413 dated Oct. 23, 2015.

* cited by examiner

*Primary Examiner* — Bin Shen
(74) *Attorney, Agent, or Firm* — Hahn Loeser & Parks, LLP

(57) ABSTRACT

Disclosed is a method for synthesizing diglyceride using a bubble column reactor. The method comprises the steps of: an immobilized enzyme is placed on the bearing mechanism of the bubble column reactor; a hot bath mechanism is actuated to heat the reactor body to 55-75° C.; glycerol, fatty acid and water are added into a feed chute, preheated to 55-75° C., and then transferred into the reactor body to initiate the reaction; a bubbling mechanism is actuated so that the inert gas is continuously blown into the reactor body via a sieve plate, forming boiling-like bubbles which promotes the mixing and hence to facilitate the reaction; after the reaction, the water bath mechanism and the bubbling mechanism are turned off, the heating and the inert gas circulation are stopped, a compacting mechanism is actuated, and the reaction mixture is settled and layered, thus obtaining an upper layer which is the crude glyceride layer, and a lower layer which is the glycerol layer; and the crude glyceride layer is subjected to two-stage molecular distillation so as to obtain high purity diglyceride.

6 Claims, 5 Drawing Sheets

US 10,138,501 B2

METHOD FOR PREPARING DIGLYCERIDE USING BUBBLE COLUMN REACTOR

CROSS-REFERENCE TO RELATED APPLICATIONS

The present application is a U.S. National Stage entry under 35 U.S.C. § 371 of International Application No. PCT/CN2015/085057 filed on Jul. 24, 2015, designating the United States of America and published in Chinese on Feb. 18, 2016, which in turn claims priority to Chinese Application 201410397931.X filed on Aug. 13, 2014, both of which are hereby incorporated by reference in their entirety.

TECHNICAL FIELD

The present invention belongs to the field of preparing food emulsifier, particularly relates to a method for preparing diglyceride using a bubble column reactor.

BACKGROUND

Diglyceride is a product obtained by the esterification of one glycerin (glycerol) molecule with two fatty acid molecules. It is a natural ingredient in oils and fats, but its content in the edible oil is often low, generally less than 10%. It is an important member of polyol-type nonionic surfactants and has various advantages, such as good safety, high nutrition value, better processing adaptability, high compatibility with the human body, etc. Therefore, it is a kind of multifunctional additive with a wide range of applications in food, medicine and chemical (cosmetics) industries. At the same time, diglyceride has a unique physiological activity—it can inhibit the diseases, such as obesity, hypertension, heart disease, etc. Therefore, it has attracted a lot of attentions in recent years.

Diglyceride can be obtained by chemical methods, but in recent years, enzymatic methods are also used because of their pros including mild reaction conditions, high specificity, and being environment-friendly. A large number of studies have been conducted on the methods of synthesizing diglyceride by enzymatic reaction in batch modes, e.g., currently the most well-studied one is the batch kettle reactor. In addition, the method for continuous production of diglyceride, i.e. production of diglyceride by a packed column reactor, also attracts a lot of attentions.

As for the batch reactions, the substrate and the biocatalyst (generally immobilized enzyme) are added into the reactor. After reaction, the product is taken out, and the catalyst enzyme is collected by filtration for reuse. However, the enzyme particle used in this method cannot be packed densely. Also, the reaction process is accompanied with strong stirring, and the shear force generated by stirring can destroy the enzyme protein, denaturing and inactivating the enzyme and thus reduces the service life.

As for the packed-bed reactor, the biocatalyst immobilized enzyme is packed uniformly in the reactor, then the reaction substrate is introduced into the reactor in a plug flow form at a volume flow rate, after circulation and reaction are carried out for a certain period of time, the reaction product is collected. As there are no back-mixing in the reactor, it is suitable for the continuous production of biological enzymatic conversion of the immobilized enzyme and the low viscosity reaction substrate. However, in this system, as the reaction proceeds, water, as a by-product, will be accumulated gradually in the reactor, which not only can reduce the esterification rate, but also hydrolyze the esterification product because water will also compete with glycerol for the acylase intermediate. In addition, the excess water will be adsorbed into the immobilized enzyme, thus reducing the activity of the enzyme. The reactor is suitable for the reaction in a homogeneous system, but is not suitable for a reaction in a heterogeneous system, because the two-phase stirring can not be carried out in the packed bed.

SUMMARY OF THE INVENTION

In order to solve the above deficiencies in the prior art, the purpose of the present invention is to provide a method for preparing diglyceride using a bubble column reactor.

The object of the present invention is achieved by the following technical solution: a method for synthesizing diglyceride using a bubble column reactor, comprising the steps of:

(1) An immobilized enzyme is placed on the bearing mechanism of a bubble column reactor; and a hot bath mechanism is actuated to heat the reactor body to 55-75° C.

(2) Glycerol and fatty acid are added into the feed chute as reactants, and water is added as an activating enzyme catalyst; wherein the molar ratio of glycerol and fatty acid is 1:1-10:1; the added amount of water is equivalent to 0-10% of the total mass of the reactants; and the added amount of the immobilized enzyme in step (1) is 1-10% of the total mass of the reactants.

(3) The glycerin, fatty acid and water in the feed chute are preheated to 55-75° C., then charged into the reactor body to initiate a synthesis reaction; and a blowing mechanism is actuated and the flow rate of the inert gas is controlled at 0.7-5.7 cm/s, so that the inert gas is continuously blown into the reactor body via the sieve plate, forming boiling bubbles.

(4) After the synthesis reaction is carried out for 15-90 min, the water bath mechanism and the blowing mechanism are turned off, and the heating and the inert gas circulation are stopped, a compacting mechanism is actuated, and the reaction mixture is stood and layered, thus obtaining an upper layer, which is a crude glycerin layer, and a lower layer, which is a glycerol layer; the crude glycerin layer is removed off the free fatty acid via a first-stage molecular distillation, then is sent into a second-stage molecular distillation so as to obtain a distillate and a distillation residue; wherein the distillate is a high purity diglyceride, and the distillation residue is a monoglyceride.

The immobilized enzyme in step (1) is Lipozyme 435; the amount of the immobilized enzyme added is 5% of the total mass of the reactants; and the reactor body is heated to 60° C.

The fatty acid in step (2) is palmitic acid, oleic acid, linoleic acid, or stearic acid; the molar ratio of glycerol and fatty acid is 7.5:1, and the added amount of water is equivalent to 2.5% of the total mass of the reactants.

The glycerol, fatty acid and water in the feed chute in step (3) are preheated to 60° C.; and the flow rate of the inert gas is 0.83 cm/s; wherein the inert gas is nitrogen.

The time for the synthesis reaction in step (4) is 30 min; the time for standing and layering is 30-60 min; the first-stage molecular distillation has a distillation temperature of 150-200° C., and a pressure of 5.0 Pa, the first-stage molecular distillation has an internal condenser temperature set to 50° C., the feeds are continuously charged, the free fatty acid is distilled off, and condensed in the condenser, then enriched as a light phase by-product; glyceride, as an undistilled heavy phase, is sent into a second-stage molecular distillation; the second-stage molecular distillation has a distillation temperature of 190-200° C., and a pressure of 1.0-3.0 Pa, the second-stage molecular distillation has an internal condenser temperature set at 50° C., the feeds are continuously charged, the fatty acid monoglyceride is distilled off and condensed in the condenser, then collected as a light phase by-product, and the heavy phase is a high purity diglyceride; wherein the high purity diglyceride has a diester content of 58.46%, with a purity of ≥90%.

The free fatty acid distilled off in the first-stage molecular distillation in step (4), can be sent back to the reaction in step (2), as a raw material. The lower layer is glycerol in the glycerol layer, which can be sent back to the reaction in step (2), as a raw material.

The first-stage molecular distillation in step (4) has a distillation temperature of 150° C., and a pressure of 5 Pa; the second-stage molecular distillation has a temperature of 200° C., and a pressure of 0.5 Pa.

The bubble column reactor in step (1) comprises a reactor body, a bearing mechanism, a sieve plate, the compacting mechanism, a blowing mechanism, a hot bath mechanism, a feed chute and a connecting cylinder, wherein the reactor body, the bearing mechanism and the connecting cylinder are connected sequentially from top to bottom; the hot bath mechanism, the reactor body and the feed chute are connected sequentially and formed a hot bath circulation; the reactor body is communicated with the connecting cylinder, the connecting cylinder is connected to the blowing mechanism, the sieve plate is arranged on the upper end of the connecting cylinder, the compacting mechanism is mounted on the connecting cylinder, the upper end of the compacting mechanism is inserted into the connecting cylinder, and the upper end of the compacting mechanism is abutted against the sieve plate.

The compacting mechanism comprises a floating joint, a cylinder, and a compacting head, wherein the piston rod of the cylinder is connected to the compacting head via the floating joint, and the compacting head is abutted against the sieve plate.

The upper end of the compacting head is provided with a first upper cavity, wherein the first upper cavity is communicated with the internal cavity of the reactor body via the sieve plate, and the bottom surface of the first upper cavity is arranged in an inclined mode; the lower end of the compacting head is provided with an first lower cavity, wherein the floating joint is connected to the first lower cavity; the side wall of the upper end of the compacting head is provided with a first through hole, wherein the first through hole is communicated with the first upper cavity and the internal cavity of the connecting cylinder.

A flow-guiding plate is provided in the internal cavity of the connecting cylinder, wherein the internal cavity of the connecting cylinder is divided into a second upper cavity and a second upper cavity by the flow-guiding plate, the second upper cavity is communicated with the internal cavity of the reactor body, the flow-guiding plate is arranged in an inclined mode, the middle of the flow-guiding plate is provided with a second through hole through which the piston rod of the cylinder passes, the floating joint is sleeved with a sealing sleeve, the sealing sleeve is closely connected to the second through hole; the connecting cylinder is provided with a gas ventilating hole and a liquid collecting hole, both the gas ventilating hole and the liquid collecting hole are communicated with the second upper cavity, and the gas ventilating hole is connected to the blowing mechanism.

The axis of the liquid collecting hole is arranged in parallel with the flow-guiding plate, the lower end of the flow-guiding plate is at the same height as that of the lower edge of the liquid collecting hole.

The blowing mechanism comprises a gas circulation booster, a condenser, a buffer tank gas and an air compressor, wherein one end of the condenser is connected to the upper end of the reactor body, the other end of the condenser is connected to the gas circulation booster, a gas bottle for storing the inert gas is connected between the condenser and the gas circulation booster; the gas circulation booster is connected to the gas ventilating hole via the buffer tank; and the air compressor is connected to the gas circulation booster, at the same time the air compressor is connected to the cylinder.

The hot bath mechanism is a water bath mechanism, wherein the water bath mechanism comprises a bathtub, a preheater and a hot water tank, the bathtub is sleeved on the reactor body, the upper end of the bathtub is connected to one end of the hot water tank via the feed chute, and the other end of the hot water tank is connected to the lower end of the bathtub via the preheater.

The hot bath mechanism is an oil bath, wherein the oil bath mechanism comprises a bathtub, a preheater and an oil tank, the bathtub is sleeved on the reactor body, the upper end of the bathtub is connected to one end of the oil tank via the feed chute, and the other end of the oil tank is connected to the lower end of the bathtub via the preheater.

The buffer tank is connected to the gas ventilating hole via the preheater.

The bearing mechanism comprises a bearing seat and a bearing cup, wherein the bearing cup is placed on the bearing seat, the reactor body, the bearing seat and the connecting cylinder are connected together via bolts, the bearing cup is inserted into the lower end of the reactor body; the bearing cup comprises a cylinder body of which the upper end and the lower end are communicated, and a screen, and the screen is fixed to the lower end of the cylinder body.

As compared with the prior art, the invention has the following advantages and beneficial effects:

(1) after the reaction of the present invention is completed, the immobilized enzyme is not necessary to be taken out, and can be reused for many times, thus reducing the reaction costs; when the reaction times is up to 30 times, the enzyme still has a high catalytic activity, with an esterification rate of 87.45%, and an DAG content of 45.64 wt %;

(2) in the present invention, the blowing mechanism and the sieve plate are combined, to blow into the reactor body, and form a gas circulation, so that the enzyme-catalyzed esterification reaction is carried out in a boiling state, nitrogen, as an inert gas, is used as a reaction protection gas, and promotes the sufficient mixing between the reaction raw materials, and between the raw materials and the enzyme, reduces the damaging effect of shear force on the enzyme, and ensures the activity of the immobilized enzyme, thus improving the reaction effect and rate of the reactants, and increasing the yield;

(3) the reaction solution can be stood or layered by centrifugation, the separation efficiency is high, and no glycerol residue remains in the glyceride layer; at the same time the glycerol layer obtained after standing the reaction solution and the by-product, a small amount of fatty acid, obtained by the first-stage molecular distillation, can be all sent back to the reaction in step (2), as raw materials;

(4) the high value-added monoglyceride by-product can be obtained from the second-stage molecular distillation

DETAILED DESCRIPTION

The present invention is further described in detail below in combination with the examples and the drawings, but the embodiments of the present invention are not limited thereto Example 1

Figure 1:
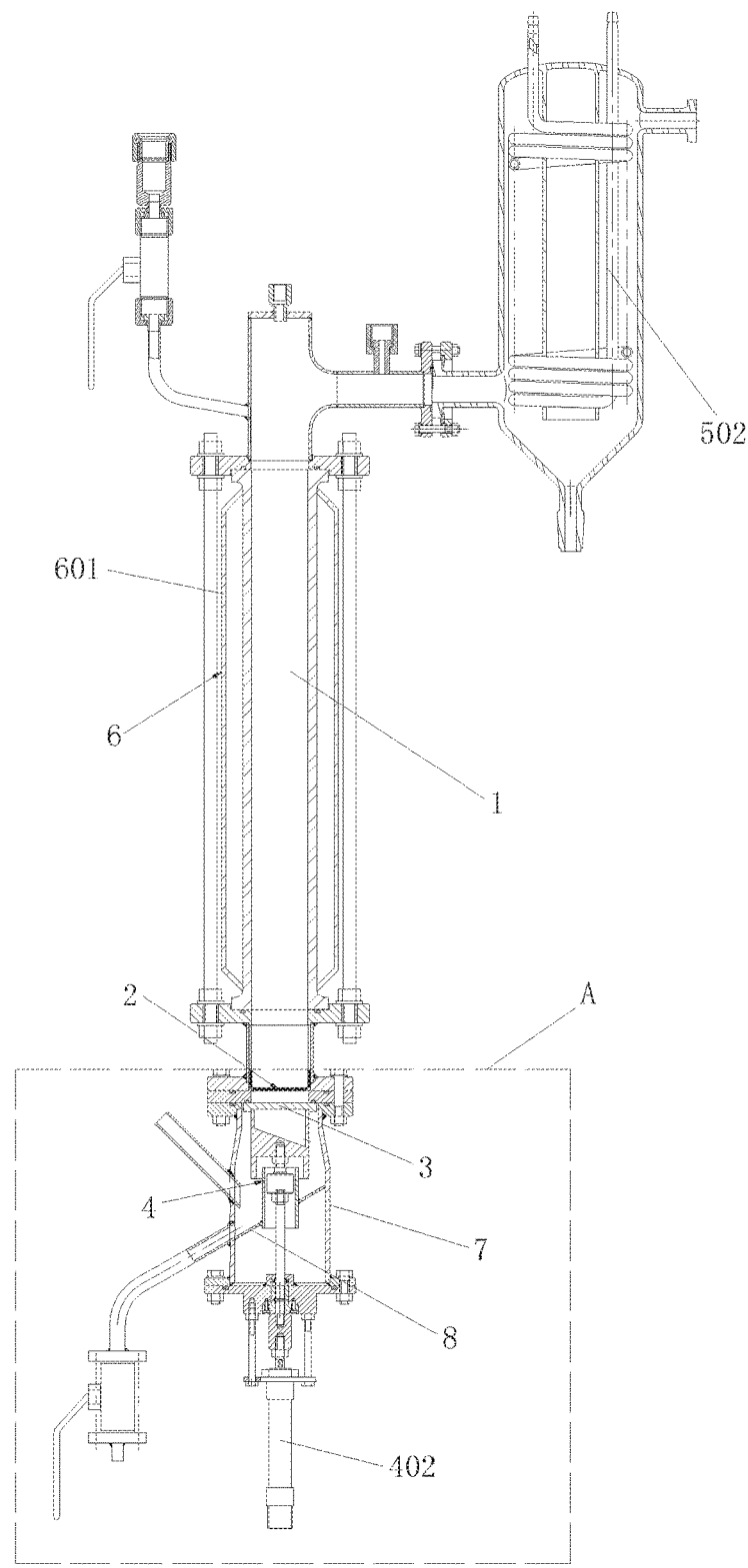
FIG. 1 is a cross-sectional view of the bubble column reactor of the present invention.
Figure 2:
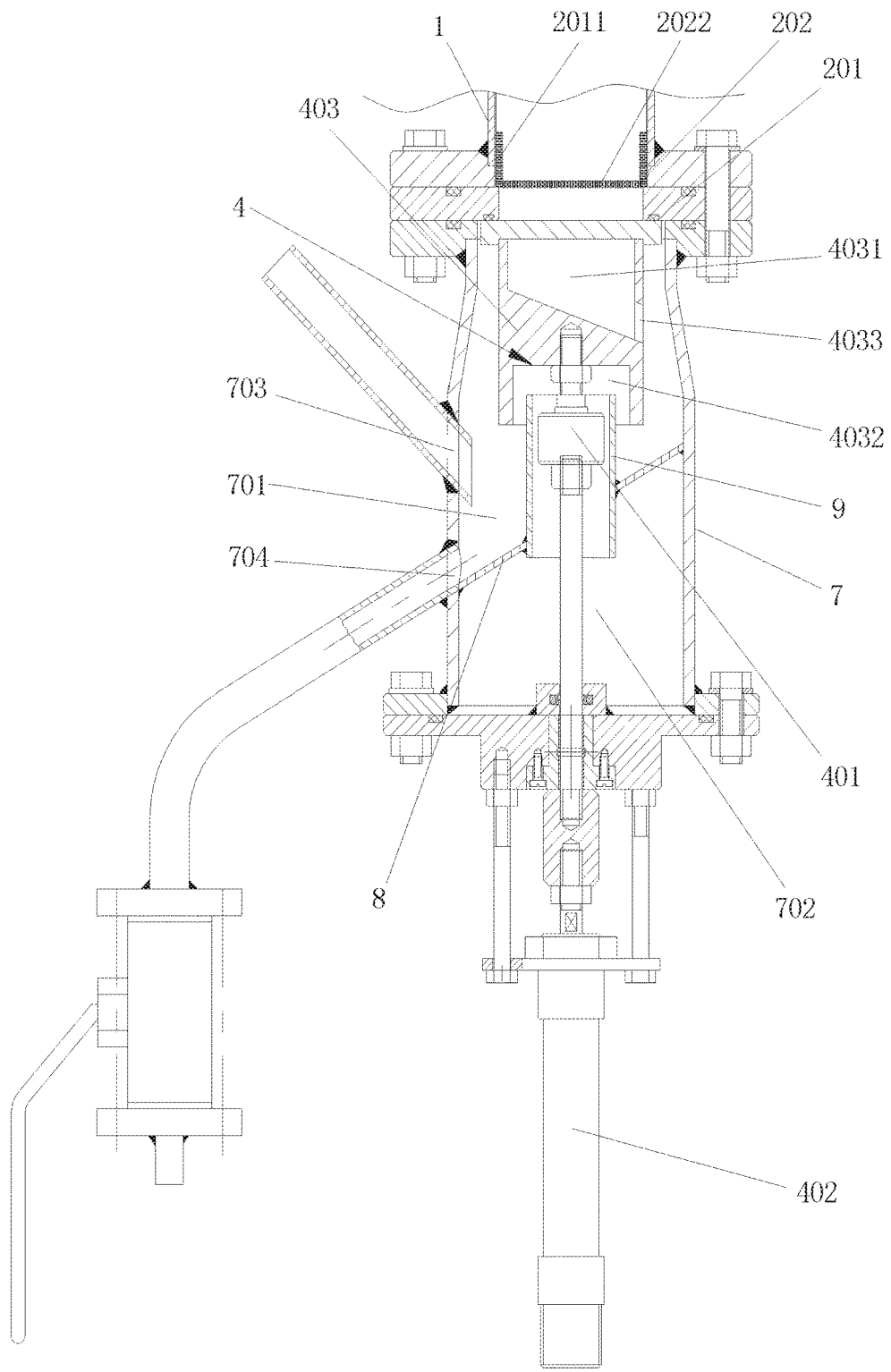
FIG. 2 is a partial enlarged view at A site in FIG. 1.
Figure 3:
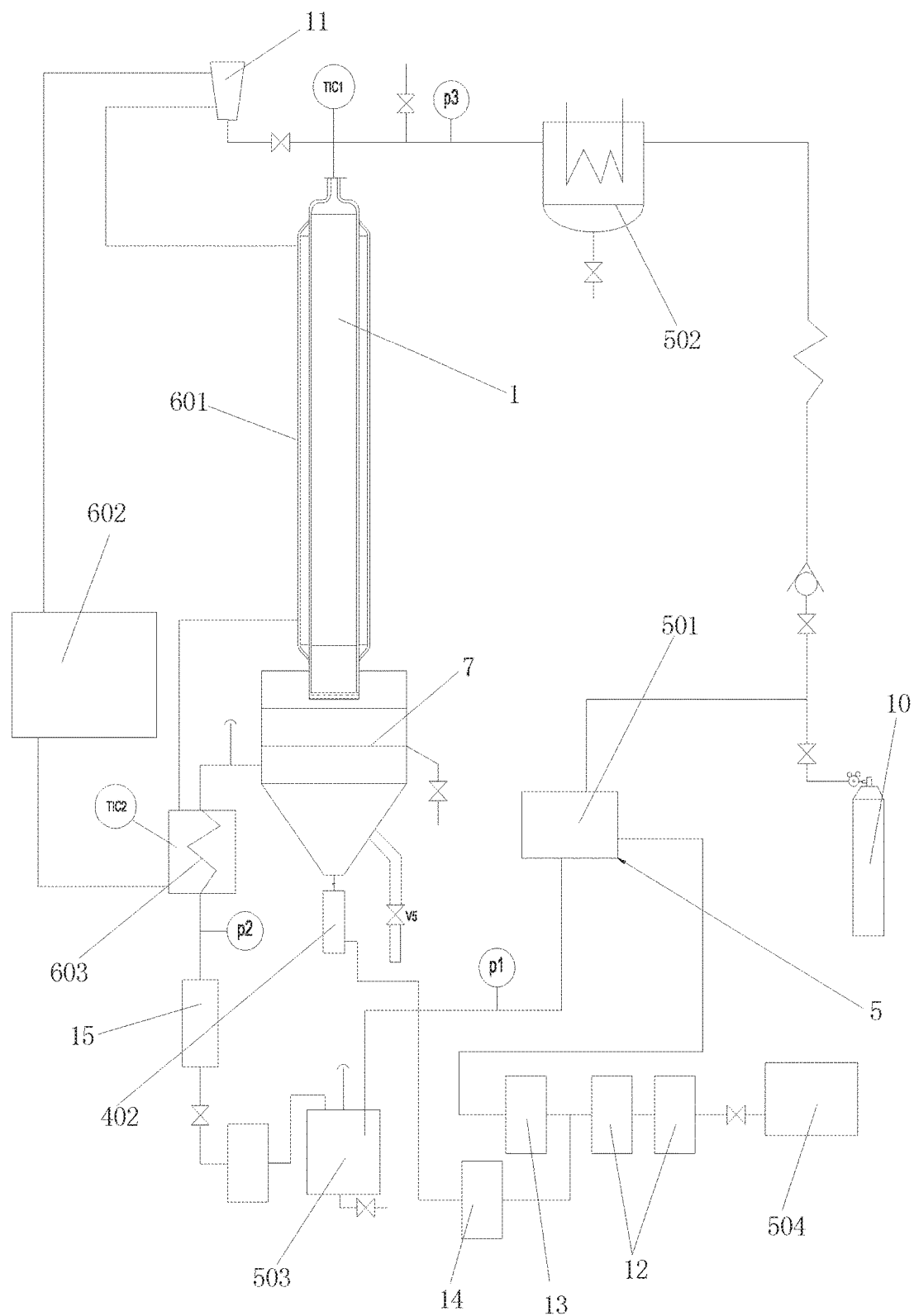
FIG. 3 is a structural schematic diagram of the bubble column reactor of the present invention.

As shown in FIG. 1, the bubble column reactor comprised a reactor body 1, a bearing mechanism 2, a sieve plate 3, a compacting mechanism 4, a blowing mechanism 5, a hot bath mechanism, a feed chute 11 and a connecting cylinder 7, wherein the reactor body 1, the bearing mechanism 2 and the connecting cylinder 7 were connected sequentially from top to bottom; the hot bath mechanism, the reactor body 1 and the feed chute 11 were sequentially connected, and formed a hot bath circulation; the reactor body 1 was communicated with the connecting cylinder 7, the connecting cylinder 7 was connected to the blowing mechanism 5, the sieve plate 3 was arranged on the upper end of the connecting cylinder 7, the compacting mechanism 4 was mounted on the connecting cylinder 7, the upper end of the compacting mechanism 4 was inserted into the connecting cylinder 7, and the upper end of the compacting mechanism 4 was abutted against the sieve plate 3.

The feed chute 11 had a bath jacket so that the reactants in the feed chute 11 can be heated via hot bath; and the sieve plate 3 had small holes, when the inert gas was blown from bottom, the sieve plate 3 can hold the highly viscous liquid reaction mixture and the solid immobilized enzyme above, so as to make them react under the bubbling state; when no gas was blown from bottom, the highly viscous liquid reaction mixture can flow out via the sieve plate 3, and be collected under the reactor.

The compacting mechanism 4 comprised a floating joint 401, a cylinder 402, and a compacting head 403, wherein the piston rod of the cylinder 402 was connected to the compacting head 403 via the floating joint 401, and the compacting head was abutted against the sieve plate 3. Such design allowed the sieve plate 3 to move up and down, thus facilitating the replacement of the sieve plate 3.

The upper end of the compacting head 403 was provided with a first upper cavity 4031, the first upper cavity 4031 was communicated with the internal cavity of the reactor body 1 via the sieve plate 3, the bottom surface of the first upper cavity 4031 was arranged in an inclined mode; the lower end of the compacting head 403 was provided with a first lower cavity 4032, the floating joint 401 was connected to the first lower cavity 4032; the side wall of the upper end of the compacting head 403 was provided with a first through hole 4033, the first through hole 4033 was communicated with the first upper cavity 4031 and the internal cavity of the connecting cylinder 7. The bottom surface of the first upper cavity 4031 was arranged in an inclined mode to prevent the products produced by the chemical reaction of the reactants in the reactor body 1 from accumulating in the first upper cavity 4031.

The flow-guiding plate 8 was provided in the internal cavity of the connecting cylinder 7, the internal cavity of the connecting cylinder 7 was divided into a second upper cavity 701 and a second upper cavity 702 by the flow-guiding plate 8, the second upper cavity 701 was communicated with the internal cavity of the reactor body 1, the flow-guiding plate 8 was arranged in an inclined mode, the middle of the flow-guiding plate 8 was provided with a second through hole through which the piston rod of the cylinder 402 passed, the floating joint 401 was sleeved with a sealing sleeve 9, the sealing sleeve 9 was closely connected to the second through hole; the connecting cylinder 7 was provided with a gas ventilating hole 703, and a liquid collecting hole 704, both the gas ventilating hole 703 and the liquid collecting hole 704 were communicated with the second upper cavity 701, the gas ventilating hole 703 was connected to the blowing mechanism 4. The flow-guiding plate 8 was provided to make the product obtained after the reaction flow out the connecting cylinder 7 smoothly, and prevent the product obtained after the reaction from accumulating in the connecting cylinder 7, thus reducing wastes.

In order to further prevent the product obtained after the reaction from flowing out the connecting cylinder 7, the axis of the liquid collecting hole 704 was arranged in parallel with the flow-guiding plate 8, and the lower end of the flow-guiding plate 8 was at the same height as that of the lower edge of the liquid collecting hole 704.

The blowing mechanism 5 comprised a gas circulation booster 501, a condenser 502, a buffer tank gas 503 and an air compressor 504, wherein one end of the condenser 502 was connected to the upper end of the reactor body 1, the other end of the condenser 502 was connected to the gas circulation booster 501, a gas bottle 10 for storing the inert gas was connected between the condenser 502 and the gas circulation booster 501; the gas circulation booster 501 was connected to the gas ventilating hole 703 via the buffer tank 503; the air compressor 504 was connected to the gas circulation booster 501, and at the same time the air compressor 504 was connected to the cylinder 402. This design not only ensured that the blowing mechanism 5 provided the reactor body 1 with sufficient gas to generate bubbles, at the same time, the gas was sent into the condenser 502 from the upper end of the reactor body 1, the gas was removed off water attached therein, then recycled again, thus reducing the cost, and reducing wastes.

In the direction from the air compressor 504 to the gas circulation booster 501, the pipeline was sequentially provided with two oil removal filters 12 and a first high pressure valve 13; and in the direction from the air compressor 504 to the cylinder 402, the pipeline was sequentially provided with two oil removal filters 12 and a second high pressure valve 14, i.e. the gas circulation booster 501 and the cylinder 402 were connected in parallel mode. The pipeline between the buffer tank 503 and the preheater 11 was provided with a flow meter 15, thus facilitating to adjust the gas pressure.

In order to further improve the reaction effect, the hot bath mechanism was a water bath mechanism 6, and the water bath mechanism 6 comprised a bathtub 601, a preheater 603 and a hot water tank 602, wherein the bathtub 601 was sleeved on the reactor body 1, the upper end of the bathtub 601 was connected to one end of the hot water tank 602 via the feed chute 11, and the other end of the hot water tank 602 was connected to the lower end of the bathtub 601 via the preheater 603.

In order to further improve the reaction efficiency, the buffer tank 503 was connected to the gas ventilating hole 705 via the preheater 603.

The bearing mechanism 2 comprised a bearing seat 201 and a bearing cup 202, the bearing cup 202 was placed on the bearing seat 201, the reactor body 1, the bearing seat 201 and the connecting cylinder 7 were connected together via bolts, the bearing cup 202 was inserted into the lower end of the reactor body 1; the bearing cup 202 comprised a cylinder body 2021, of which the upper end and the lower end were communicated, and a screen 2022, and the screen 2022 was fixed to the lower end of the cylinder body 2021.

Example 2

The present bubble column reactor was the same as that in example 1, except the following technical features: the hot bath mechanism was an oil bath mechanism, and the oil bath mechanism comprised a bathtub, a preheater and an oil tank, wherein the bathtub was sleeved on the reactor body, the upper end of the bathtub was connected to one end of the oil tank via the feed chute, the other end of the oil tank was connected to the lower end of the bathtub via the preheater; and at the same time, the buffer tank was connected to the gas ventilating hole via the preheater.

Example 3

(1). 22.75 g of immobilized enzyme Lipozyme 435 (Novozymes, Denmark) was placed on the bearing mechanism of a bubble column reactor, and a hot bath mechanism was actuated to heat the reactor body to 60° C.

(2). 129.19 g mixture of palmitic acid and oleic acid (in total 0.47 mol, the mass ratio was of 6:4), and 325.81 g glycerol (in total 3.54 mol) were added into the feed chute as reactants, and 11.375 g of water was added as an activating enzyme catalyst.

(3). The reactants and water in the feed chute were preheated to 60° C., then charged into the reactor body to initiate a synthesis reaction; and the blowing mechanism was actuated and the flow rate of the inert gas was controlled at 0.7 cm/s, so that the inert gas was continuously blown into the reactor body via the sieve plate, forming boiling bubbles.

Figure 4:
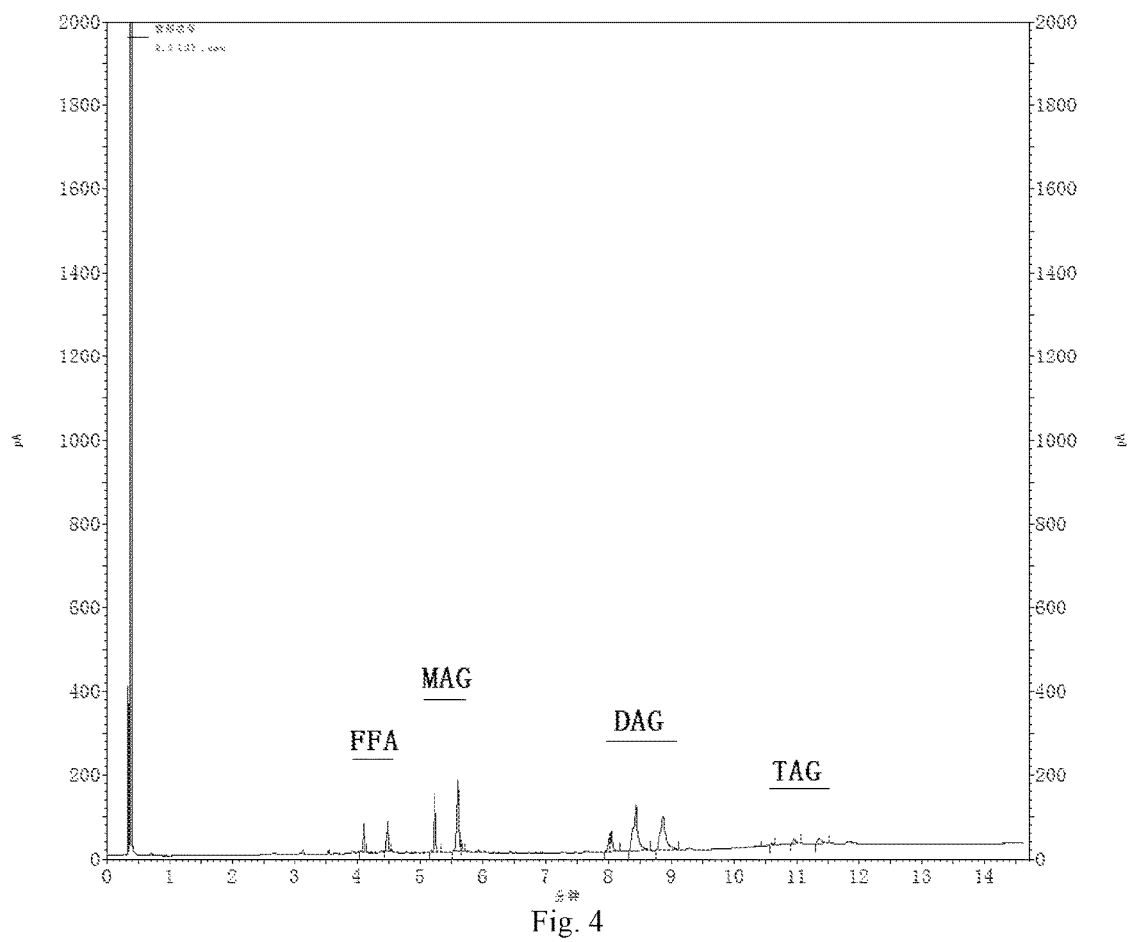
FIG. 4 is the gas chromatogram result of the glyceride obtained in example 1, where FFA is free fatty acid, MAG is monoglyceride, DAG is diglyceride, and TAG is triglyceride.

(4) After the synthesis reaction was carried out for 45 min, the water bath mechanism and the blowing mechanism were turned off, the heating and the inert gas circulation were stopped, a compacting mechanism was actuated, and the reaction mixture was stood and layered, thus obtaining an upper layer, which was a crude glycerin layer, and a lower layer, which was a glycerol layer; the glycerol layer was measured to have an esterification rate of 90.50%, and a composition of free fatty acid, monoglyceride, diglyceride and triglyceride by gas chromatography analysis, wherein the free fatty acid had a mass percentage of 9.27%, the monoglyceride had a mass percentage of 27.80%, the diglyceride had a mass percentage of 58.46%, and the triglyceride had a mass percentage of 4.47% (the gas chromatograms were shown in FIG. 4); and the glycerol layer was sent back to step (2) as a raw material.

(5) Removing free fatty acids from the glyceride layer: the glyceride layer obtained in step (1) was sent into a feed tank of the molecular distillation apparatus, the first-stage molecular distillation had a distillation temperature set at 150° C., and a pressure of 5.0 Pa, first-stage molecular distillation had an internal condenser temperature of 50° C.; the feeds were charged continuously, the free fatty acid was distilled off, and condensed in the internal condenser, then collected as a light phase by-product, and sent back to step (2) as a raw material; and glyceride, as an undistilled heavy phase, was sent into the second-stage molecular distillation continuously.

Figure 5:
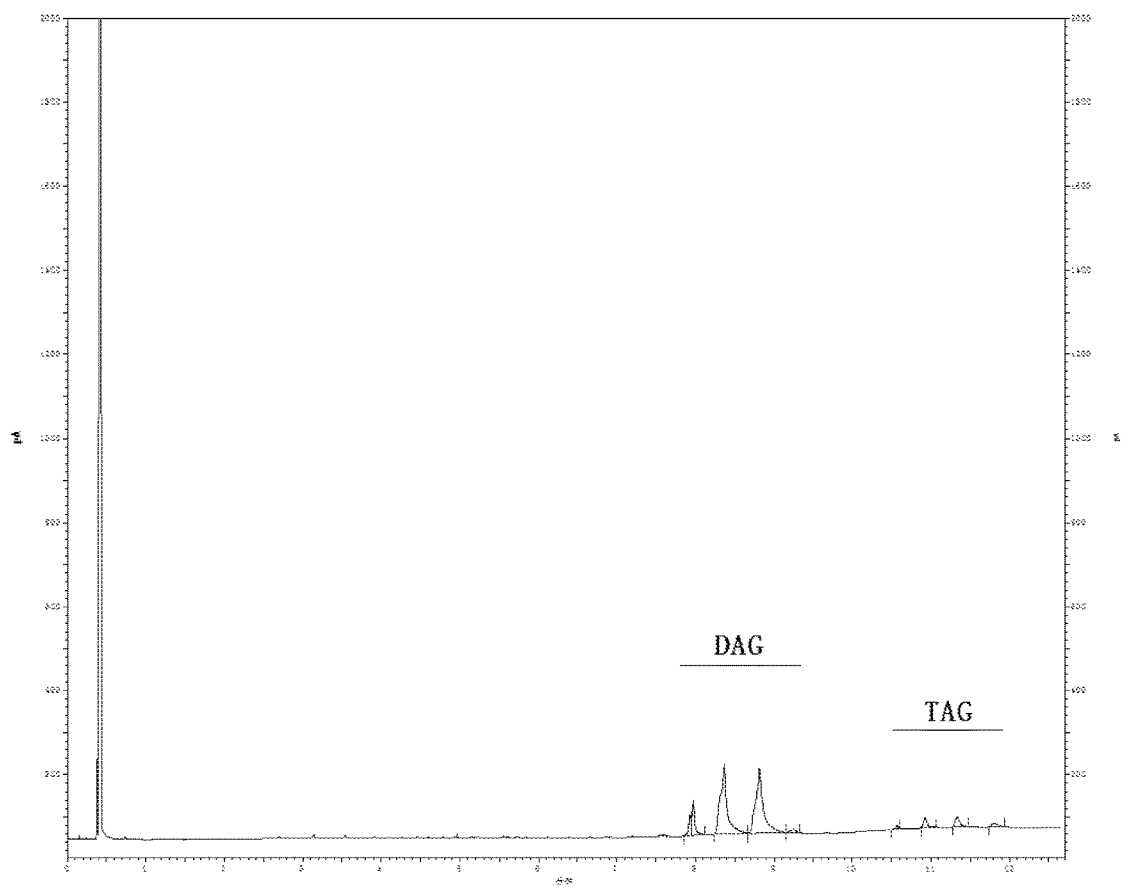
FIG. 5 is the gas chromatogram analysis results of high-purity diglyceride obtained in example 1, where DAG is diglyceride, and TAG is triglyceride.

(6) Preparation of high purity diglyceride: the glyceride in the free fatty acid-removed heavy phase obtained in step (5) was continuously sent into the second-stage molecular distillation, the second-stage molecular distillation had a temperature set at 190° C., a pressure of 1.0 Pa, and an internal condenser temperature of 50° C. The feeds were continuously charged, the fatty acid monoglyceride was distilled off, and condensed in the internal condenser, then collected as a light phase by-product, and the heavy phase was diglyceride and a small amount of triglyceride, with a diglyceride purity of 92.0% (the gas chromatograms were shown in FIG. 5).

Example 4

(1) 4.55 g of immobilized enzyme Lipozyme 435 (Novozymes, Denmark) was placed on the bearing mechanism of a bubble column reactor; and a hot bath mechanism was actuated to heat the reactor body to 60° C.

(2) 167.5 g palm oil fatty acid (containing 55% palmitic acid, 33% oleic acid, and small amounts of other fatty acids) and 287.5 g of glycerol were added into the feed chute as reactants, and 22.75 g of water was added as an activating enzyme catalyst.

(3) The reactants and water in the feed chute were preheated to 60° C., then charged into the reactor body to initiate a synthesis reaction; and the blowing mechanism was actuated and the flow rate of the inert gas was controlled at 5.7 cm/s, so that the inert gas was continuously blown into the reactor body via the sieve plate, forming boiling bubbles.

(4) After the synthesis reaction was carried out for 60 min, the water bath mechanism and the blowing mechanism were turned off, the heating and the inert gas circulation were stopped, a compacting mechanism was actuated, and the reaction mixture was stood and layered, thus obtaining an upper layer, which was a crude glycerin layer, and a lower layer, which was a glycerol layer; the glycerin layer was measured to have an esterification rate of 45.29%, and a composition of free fatty acid, monoglyceride, diglyceride and triglyceride by gas chromatography analysis, wherein, the free fatty acid had a mass percentage of 66.36%, the monoglyceride had a the mass percentage of 5.61%, the diglyceride had a mass percentage of 27.61%, and the triglyceride had a mass percentage of 0.42%; and the glycerol layer was sent back to step (2) as a raw material.

(5) Removing free fatty acid from the glyceride layer: the glyceride layer obtained in step (1) was sent into the feed tank of the molecular distillation apparatus, the first-stage molecular distillation had a distillation temperature set at 200° C., and a pressure of 5.0 Pa, the first-stage molecular distillation had an internal condenser temperature of 50° C.; the feeds were continuously charged, the free fatty acid was distilled off, and condensed in the internal condenser, then collected as a light phase by-product, and sent back to step (2) as a raw material. Glyceride, as undistilled heavy phase, was continuously sent into the second-stage molecular distillation.

(6) Preparation of high purity diglyceride: the glyceride of the free fatty acid-removed heavy phase obtained in step (5) was continuously sent into the second-stage molecular distillation, and the second-stage molecular distillation had a temperature set at 200° C., a pressure of 3.0 Pa, and an internal condenser temperature of 50° C. The feeds were continuously charged, fatty acid monoglyceride was distilled off, and condensed in the internal condenser, then collected as a light phase product, and the heavy phase was diglyceride and a small amount of triglyceride, with a diglyceride purity of 91.42%.

Example 5

(1) 22.75 g of immobilized enzyme Lipozyme 435 (Novozymes, Denmark) was placed on the bearing mechanism of a bubble column reactor; and a hot bath mechanism was actuated to heat reactor body to 60° C.

(2) 129.19 g of oleic acid and 325.81 g glycerol were added into the feed chute as reactants, and 11.375 g of water was added as an activating enzyme catalyst.

(3) The reactants and water in the feed chute were preheated to 60° C., then charged into the reactor body to initiate a synthesis reaction; and the blowing mechanism was actuated and the flow rate of the inert gas was controlled at 2.0 cm/s, so that the inert gas was continuously blown into the reactor body via the sieve plate, forming boiling bubbles.

(4) After the synthesis reaction is carried out for 30 min, the water bath mechanism and the blowing mechanism were turned off, the heating and inert gas circulation were stopped, a compacting mechanism was actuated, and the reaction mixture was stood and layered, thus obtaining an upper layer, which was a crude glycerin layer, and a lower layer, which was a glycerol layer; the glyceride layer was measured to have an esterification rate of 90.80%, and a composition of free fatty acid, monoglyceride, diglyceride and triglyceride by gas chromatography analysis, wherein, the free fatty acid had a mass percentage of 9.89%, the monoglyceride had a mass percentage of 34.76%, the diglyceride had a mass percentage of 50.31%, and triglyceride had a mass percentage of 5.04%; and the glycerol layer was sent back to step (2) as a raw material.

(5) Removing free fatty acid from the glyceride layer: the glyceride layer obtained in step (1) was sent into the feed tank of the molecular distillation apparatus, the first-stage molecular distillation had a distillation temperature set at 150° C., and a pressure of 5.0 Pa, the first-stage molecular distillation had an internal condenser temperature of 50° C.; the feeds were continuously charged, the free fatty acid was distilled off, and condensed in the internal condenser, then collected as a light phase by-product, and was sent back to step (2) as a raw material. Glyceride, as undistilled heavy phase, was continuously sent into the second-stage molecular distillation.

(6) Preparation of high purity diglyceride: the glyceride in the free fatty acid-removed heavy phase obtained in step (5) was continuously sent into the second-stage molecular distillation, the second-stage molecular distillation had a temperature set at 190° C., a pressure of 2.0 Pa, and an internal condenser temperature of 50° C. The feeds were continuously charged, the fatty acid monoglyceride was distilled off, and condensed in the internal condenser, then collected as a light phase product, and the heavy phase was diglyceride and a small amount of triglyceride, with a diglyceride purity 90.08%.

Example 6

(1) 34.125 g immobilized enzyme Lipozyme 435 (Novozymes, Denmark) was placed on the bearing mechanism of a bubble column reactor; and a hot bath mechanism was actuated to heat the reactor body to 65° C.

(2) 125 g of stearic acid and 325.81 g glycerol were added into the feed chute as reactants, and 11.375 g of water was added as an activating enzyme catalyst.

(3) The reactants and water in the feed chute were pre-heated to 65° C., then charged into the reactor body to initiate a synthesis reaction; and the blowing mechanism was actuated and the flow rate of the inert gas was controlled at 3.0 cm/s, so that the inert gas was continuously blown into the reactor body via the sieve plate, forming boiling bubbles.

(4) After the synthesis reaction was carried out for 90 min, the water bath mechanism and the blowing mechanism were turned off, the heating and the inert gas circulation were stopped, a compacting mechanism was actuated, and the reaction mixture was stood and layered, thus obtaining an upper layer, which was a crude glycerin layer, and a lower layer, which was a glycerol layer; the glyceride layer was measured to have an esterification rate of 89.75%, and a composition of free fatty acid, monoglyceride, diglyceride and triglyceride by gas chromatography analysis, wherein, the free fatty acid had a mass percentage of 11.97%, the monoglyceride had a mass percentage of 38.8%, the diglyceride had a mass percentage of 46.3%, and the triglyceride had a mass percentage of 2.93%; and the glycerol layer was sent back to step (2) as a raw material.

(5) Removing free fatty acid from the glyceride layer: the glyceride layer obtained in step (1) was sent into the feed tank of the molecular distillation apparatus, the first-stage molecular distillation had a distillation temperature set at 200° C., and a pressure of 5.0 Pa, the first-stage molecular distillation had an internal condenser temperature of 50° C.; the feeds were continuously charged, the free fatty acid was distilled off, and condensed in the internal condenser, then collected as a light phase by-product, and was sent back to step (1) as a raw material. Glyceride, as an undistilled heavy phase, was continuously sent into the second-stage molecular distillation.

(6) Preparation of high purity diglyceride: the glyceride in the free fatty acid-removed heavy phase obtained in step (2) was continuously sent into the second-stage molecular distillation, the second-stage molecular distillation had a temperature set at 190° C., a pressure of 1.0 Pa, and an internal condenser temperature of 50° C. The feeds were continuously charged, the fatty acid monoglyceride was distilled off, and condensed in the internal condenser, then collected as a light phase product, and the heavy phase was diglyceride and a small amount of triglyceride, with a diglyceride purity of 90.48%.

The above examples are the preferred embodiments of the present invention, but the embodiments of the present invention are not limited to the examples described above, any other change, modification, alternative, combination, simplification, made without departing from the spirit and the principle of the invention, all of which should be the equivalent replacement mode, will be included within the scope of the present invention.

The invention claimed is:
1. A method for synthesizing diglyceride using a bubble column reactor, characterized by comprising the steps of:
(1) placing an immobilized enzyme on the bearing mechanism of the bubble column reactor, and a hot bath mechanism is actuated to heat the reactor body to 55-75° C.;
(2) adding glycerol and fatty acid in a feed chute as reactants, and water is added as an activating enzyme catalyst; wherein the molar ratio of glycerol and fatty acid is 1:1-10:1; the added amount of water is less than 10% of the total mass of the reactants; and the added amount of the immobilized enzyme in step (1) is 1-10% of the total mass of the reactants;

(3) preheating glycerin, fatty acids and water in the feed chute to 55-75° C., then charged into the reactor body to initiate a synthesis reaction; a blowing mechanism is actuated and the flow rate of an inert gas is controlled at 0.7-5.7 cm/s, so that the inert gas is continuously blown into the reactor body via a sieve plate, forming boiling bubbles;

(4) turning off the hot bath mechanism and the blowing mechanism after the synthesis reaction is carried out for 15-90 min, stopping the heating and the inert gas circulation, actuating a compacting mechanism, and standing and layering the reaction mixture, thus obtaining an upper layer, which is a crude glycerin layer, and a lower layer, which is a glycerol layer; the crude glycerin layer is removed off the free fatty acids via a first-stage molecular distillation, then sent into a second-stage molecular distillation, thus obtaining a distillate and a distillation residue; wherein the distillate is high purity diglyceride, and the distillation residue is monoglyceride;

wherein the bubble column reactor in step (1) comprises a reactor body, a bearing mechanism, a sieve plate, a compacting mechanism, a blowing mechanism, a hot bath mechanism, a feed chute, and a connecting cylinder, wherein the reactor body, the bearing mechanism and the connecting cylinder are connected sequentially from top to bottom; the hot bath mechanism, the reactor body, and feed chute are sequentially connected, and formed a hot bath circulation; the reactor body is communicated with the connecting cylinder, the connecting cylinder is connected to the blowing mechanism, the sieve plate is placed on the upper end of the connecting cylinder, the compacting mechanism is mounted on the connecting cylinder, the upper end of the compacting mechanism is inserted into the connecting cylinder, and the upper end of the compacting mechanism is abutted against the sieve plate;

wherein the compacting mechanism comprises a floating joint, a cylinder, a compacting head, wherein the piston rod of the cylinder is connected to the compacting head via the floating joint, the compacting head is abutted against the sieve plate; the upper end of the compacting head is provided with a first upper cavity, the first upper cavity is communicated with the internal cavity of the reactor body via the sieve plate, the bottom surface of the first upper cavity is arranged in an inclined mode; the lower end of the compacting head is provided with a first lower cavity, the floating joint is connected to the first lower cavity; the side wall of the upper end of the compacting head is provided with a first through hole, the first through hole is communicated with the first upper cavity and the internal cavity of the connecting cylinder; and wherein the internal cavity of the connecting cylinder is provided with flow-guiding plate, the internal cavity of the connecting cylinder is divided into a second upper cavity and the second upper cavity by the flow-guiding plate, the second upper cavity is communicated with the internal cavity of the reactor body, the flow-guiding plate is arranged in an inclined mode, the middle of the flow-guiding plate is provided with a second through hole through which the piston rod of the cylinder passes, the floating joint is sleeved with a sealing sleeve, the sealing sleeve is closely connected to the second through hole; the connecting cylinder is provided with a gas ventilating hole and a liquid collecting hole, both the gas ventilating hole and the liquid collecting hole are communicated with the second upper cavity, the gas ventilating hole is connected to the blowing mechanism; the axis of the liquid collecting hole is arranged in parallel with the flow-guiding plate, and the lower end of the flow-guiding plate is at the same height as that of the lower edge of the liquid collecting hole.

2. The method according to claim 1, characterized in that:
the immobilized enzyme in step (1) is immobilized lipase from *Candida antarctica*, the added amount of the immobilized enzyme is 5% of the total mass of the reactants; and the reactor body is heated to 60° C.;
the fatty acid in step (2) is palmitic acid, oleic acid, linoleic acid, or stearic acid; the molar ratio of glycerol and fatty acid is 7.5:1; and the added amount of water is equivalent to 2.5% of the total mass of the reactants;
glycerin, fatty acid and water in the feed chute in step (3) are preheated to 60° C.; the flow rate of the inert gas is 0.83 cm/s; and the inert gas is nitrogen;
the time for the synthesis reaction in step (4) is 30 min, the time for standing and layering is 30-60 min; the first-stage molecular distillation has a distillation temperature of 150-200° C., and a pressure of 1-20 Pa, the first-stage molecular distillation has an internal condenser temperature set at 50° C., the feeds are charged continuously, the free fatty acid is distilled off, and condensed in a condenser, then enriched as a light phase by-product; the glyceride, as an undistilled heavy phase, is sent into the second-stage molecular distillation; the second-stage molecular distillation has a distillation temperature of 190-200° C. and a pressure of 0.1-5 Pa, the second-stage molecular distillation has an internal condenser temperature set at 50° C., feeds are charged continuously, the fatty acid monoglyceride is distilled off, condensed in the condenser, then collected as a light phase by-product, the heavy phase is high purity diglyceride; wherein the high purity diglyceride has a diester content of 58.46%, and a purity of ≥90%.

3. The method according to claim 1, characterized in that the first-stage molecular distillation in step (4) has a distillation temperature of 150° C., and a pressure of 5 Pa; and the second-stage molecular distillation has a temperature of 200° C. and a pressure of 0.5 Pa.

4. The method according to claim 1, characterized in that the blowing mechanism comprises a gas circulation booster, a condenser, a buffer tank gas, and an air compressor, wherein one end of the condenser is connected to the upper end of the reactor body, the other end of the condenser is connected to the gas circulation booster, a gas bottle for storing the inert gas is connected between the condenser and the gas circulation booster; the gas circulation booster is connected to the gas ventilating hole via the buffer tank; the air compressor is connected to the gas circulation booster, and at the same time the air compressor is connected to the cylinder.

5. The method according to claim 4, characterized in that the hot bath is a water bath mechanism, and the water bath mechanism comprises a bathtub, a preheater, and a hot water tank, wherein the bathtub is sleeved on the reactor body, the upper end of the bathtub is connected to one end of the hot water tank via the feed chute, and the other end of the hot water tank is connected to the lower end of the bathtub via the preheater; and the buffer tank is connected to the gas ventilating hole through the preheater.

6. The method according to claim 1, characterized in that the bearing mechanism comprises a bearing seat and a bearing cup, wherein the bearing cup is placed on the bearing seat, the reactor body, the bearing seat, and the connecting cylinder are connected together via bolts, the bearing cup is inserted into the lower end of the reactor body; the bearing cup comprises a cylinder body, of which the upper end and the lower end are communicated, and a screen, and the screen is fixed to the lower end of the cylinder body.

* * * * *